United States Patent
Li et al.

(10) Patent No.: US 10,155,106 B2
(45) Date of Patent: Dec. 18, 2018

(54) METHOD FOR MAKING IMPLANTABLE LEAD

(71) Applicant: Tsinghua University, Beijing (CN)

(72) Inventors: Lu-Ming Li, Beijing (CN);
Chang-Qing Jiang, Beijing (CN);
Hong-Wei Hao, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 2 days.

(21) Appl. No.: 15/345,222

(22) Filed: Nov. 7, 2016

(65) Prior Publication Data

US 2017/0054263 A1    Feb. 23, 2017

Related U.S. Application Data

(62) Division of application No. 13/749,649, filed on Jan. 24, 2013.

(30) Foreign Application Priority Data

Sep. 7, 2012 (CN) .......................... 2012 1 0330922

(51) Int. Cl.
*A61N 1/05* (2006.01)
*A61N 1/08* (2006.01)
(Continued)

(52) U.S. Cl.
CPC .......... *A61N 1/05* (2013.01); *H01R 13/6599* (2013.01); *H01R 24/58* (2013.01); *A61N 1/086* (2017.08);
(Continued)

(58) Field of Classification Search
CPC .......... A61N 1/056–1/057; A61N 1/05; A61N 1/086; Y10T 29/49117; Y10T 29/49208; H01R 2201/12
See application file for complete search history.

(56) References Cited

U.S. PATENT DOCUMENTS

| 4,437,474 A | 3/1984 | Peers-Trevarton |
| 4,458,695 A | 7/1984 | Peers-Trevarton |

(Continued)

FOREIGN PATENT DOCUMENTS

| CN | 1388540 | 1/2003 |
| CN | 101109098 | 1/2008 |

(Continued)

OTHER PUBLICATIONS

Final Office Action on co-pending (U.S. Appl. No. 13/749,649) dated Aug. 5, 2016.
(Continued)

*Primary Examiner* — Livius Radu Cazan

(57) ABSTRACT

A method for making an implantable lead is related. A pipe is provided. The pipe includes a first end portion, a second end portion opposite to the first end portion, and a middle portion connecting the first end portion and the second end portion. A flexible conductive layer is formed on the middle portion of the pipe. At least one contactor is applied on the first end portion of the pipe. At least one connector is applied on the second end portion of the pipe. At least one wire is placed in the pipe to electrically connect the at least one contactor and the at least one connector.

13 Claims, 19 Drawing Sheets

(51) Int. Cl.
*H01R 24/58* (2011.01)
*H01R 13/6599* (2011.01)

(52) U.S. Cl.
CPC ..... *H01R 2201/12* (2013.01); *Y10T 29/49208* (2015.01)

(56) References Cited

U.S. PATENT DOCUMENTS

| | | | |
|---|---|---|---|
| 4,600,017 | A | 7/1986 | Schroeppel |
| 4,608,986 | A * | 9/1986 | Beranek ................. A61N 1/056 607/123 |
| 5,336,254 | A | 8/1994 | Brennen et al. |
| 5,411,527 | A | 5/1995 | Alt |
| 5,411,544 | A | 5/1995 | Mar et al. |
| 5,683,444 | A * | 11/1997 | Huntley ............... A61N 1/0565 607/122 |
| 5,702,437 | A | 12/1997 | Baudino |
| 6,181,971 | B1 * | 1/2001 | Doan ....................... A61N 1/05 607/116 |
| 6,480,747 | B2 | 11/2002 | Schmidt |
| 6,792,309 | B1 | 9/2004 | Noren |
| 6,999,821 | B2 | 2/2006 | Jenney et al. |
| 7,571,010 | B2 | 8/2009 | Zarembo et al. |
| 7,832,983 | B2 | 11/2010 | Kruckenberg et al. |
| 7,844,347 | B2 | 11/2010 | Brabec et al. |
| 7,917,213 | B2 | 3/2011 | Bulkes et al. |
| 8,127,440 | B2 | 3/2012 | Douglas |
| 8,244,346 | B2 | 8/2012 | Foster et al. |
| 8,626,315 | B2 | 1/2014 | Liu et al. |
| 8,734,437 | B2 | 5/2014 | Anderson et al. |
| 8,855,788 | B2 | 10/2014 | Lloyd et al. |
| 2004/0223900 | A1 | 11/2004 | Khabashesku et al. |
| 2005/0203604 | A1 | 9/2005 | Brabec et al. |
| 2005/0222659 | A1 | 10/2005 | Olsen et al. |
| 2006/0204427 | A1 | 9/2006 | Ghenciu et al. |
| 2007/0116631 | A1 * | 5/2007 | Li .......................... B82Y 30/00 423/447.3 |
| 2007/0208383 | A1 | 9/2007 | Williams |
| 2008/0183258 | A1 | 7/2008 | Inman |
| 2008/0195186 | A1 * | 8/2008 | Li ......................... A61N 1/0551 607/115 |
| 2008/0195187 | A1 | 8/2008 | Li et al. |
| 2010/0276633 | A1 | 11/2010 | Pick et al. |
| 2010/0331938 | A1 | 12/2010 | Sommer et al. |
| 2011/0190860 | A1 | 8/2011 | Harberts et al. |
| 2012/0011711 | A1 * | 1/2012 | Cox ......................... A61N 1/05 29/825 |
| 2014/0288618 | A1 | 9/2014 | Li et al. |

FOREIGN PATENT DOCUMENTS

| | | |
|---|---|---|
| CN | 101172184 | 5/2008 |
| CN | 101484628 | 7/2009 |
| CN | 101927057 | 12/2010 |
| CN | 102068760 | 5/2011 |
| CN | 101925379 | 7/2013 |
| CN | 102327668 | 1/2014 |

OTHER PUBLICATIONS

Non-Final Office Action on co-pending (U.S. Appl. No. 13/749,649) dated Apr. 7, 2016.
Final Office Action on co-pending (U.S. Appl. No. 13/749,649) dated Jan. 29, 2016.
Non-Final Office Action on co-pending (U.S. Appl. No. 13/749,649) dated Jul. 30, 2015.
"Electrical properties of single carbon fibres", C N Owston 1970 J. Phys. D: Appl. Phys. 3 1615.

* cited by examiner

METHOD FOR MAKING IMPLANTABLE LEAD

CROSS-REFERENCE TO RELATED APPLICATIONS

This application claims all benefits accruing under 35 U.S.C. § 119 from Chinese Patent Application No. 201210330922.X, filed on Sep. 7, 2012, in the State Intellectual Property Office of China, the disclosure of which is incorporated herein by reference, and this application is a divisional of copending application Ser. No. 13/749,649, filed on Jan. 24, 2013, which is also incorporated herein by reference.

BACKGROUND

1. Technical Field

The present disclosure relates to medical devices, in particular, to an implantable lead, a medical device using the same and a method for making the same.

2. Description of Related Art

In recent years, implantable medical devices (IMD), such as heart pacemakers, defibrillators are widely and increasingly applied in treatments of diseases. Currently, there are more than 5 million implanted patients in the world. Furthermore, deep brain stimulator (DBS) has demonstrated its remarkable success in treating movement disorders such as Parkinson's disease, essential tremor and dystonia. Also, spinal cord stimulators are widely used in the treatment of pain. Other IMD such as vagus nerve stimulator, sacral nerve stimulator, stomach stimulator, bladder stimulator have been developed and put into clinical applications.

Magnetic resonance imaging (MRI) is widely used in modern medical diagnosis because of MRI is non-radioactive, has high-resolution, capable of soft tissue imaging, and development brain function. It is estimated that the global annual MRI examination is more than 60 million times and will rise continuously. However, the risk for patients having the IMD implants, such as heart pacemaker, defibrillator, or nerve stimulator, is significant mainly due to the radio frequency (RF) heating produced during the MRI examination.

The MRI utilizes three electromagnetic fields to function. The first one is a static magnetic field $B_0$ used to provide a uniform magnetic field environment. The second one is a gradient magnetic field used to generate spatial position information. The third one is a RF magnetic field used to excite an MR signals. The RF magnetic field has a high-power and is high-frequency time-varying magnetic field. The frequency f of the RF magnetic field is determined by the Larmor formula $f=\gamma B_0$, wherein $\gamma$ is gyromagnetic ratio with a value of 42.5 Hz/T. According to Faraday's law of electromagnetic induction, changes of the RF magnetic field will induce electric fields in biological tissues. When a slender metal is implanted in a biological tissue, such as the heart pacemaker lead or the DBS lead, the slender metal will receive the RF signal like an antenna and cause an induced electric field aggregate at the tip of the slender metal to produce a severe ohmic heat which is called RF heating.

In a phantom study, a temperature rise up to 63° C. is observed and a temperature rise up to 20° C. is observed in animals when 1.5 T MRI is used to scan. Such a high temperature may cause serious harm to patients. For example, the United State Food and Drug Administration (FDA) had reported that the implantation of DBS in Parkinson patients for MRI examination leads to coma and permanent disability cases. The above risk causes about 200 thousand patients refusing the MRI examinations. However, it is reported that about 50%-70% of patients with the implants need the MRI examinations in the life cycles of the IMD.

Thus, it is important to provide a safe IMD in the MRI environment, especially in the case of heart pacemakers, defibrillators, or nerve stimulators, without RF heating resulting a severe temperature rise at the lead during the MRI examination. Since the RF heating is mainly produced at the lead, it is very useful to provide improve leads which are safe to use in the MRI environment.

Metal shielding layer is widely used in the protection of the cable by shielding the electromagnetic radiation. However, metal shielding layer structure cannot reduce RF heating effectively because of the thick insulating layer outside of the cable. Furthermore, metals with good biocompatibility are rare and expensive. Properties of a potential suitable metal are also difficult to maintain after the metal is made into thin shielding layer. In U.S. patent Publication No. U.S. 2008195187A1 published on Aug. 14, 2008, entitled "DISCONTINUOUS CONDUCTIVE FILLER POLYMER-MATRIX COMPOSITES FOR ELECTROMAGNETIC SHIELDING", filed on Feb. 14, 2007, a polymer composite is applied to the shielding layer. However, the shielding effect is relatively poor, and the shield layer needs to be made very thick to take advantage of the properties of the polymer composite, while makes the shielding layer become unsuitable for the IMD.

What is needed, therefore, is to provide an implantable lead, a medical device using the same and a method for making the same which can overcome the shortcomings described above.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

References will now be made to the drawings to describe, in detail, various embodiments of the present implantable lead, medical device using the same and method for making the same.

Figure 1A:
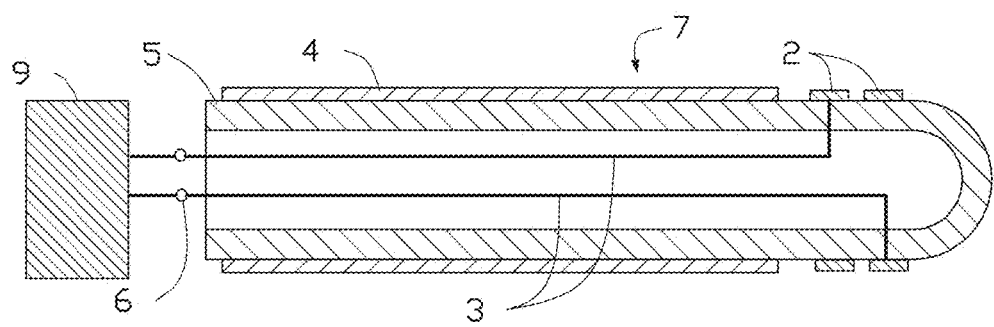
FIG. 1A is a schematic view of one embodiment of a medical device.
Figure 1B:
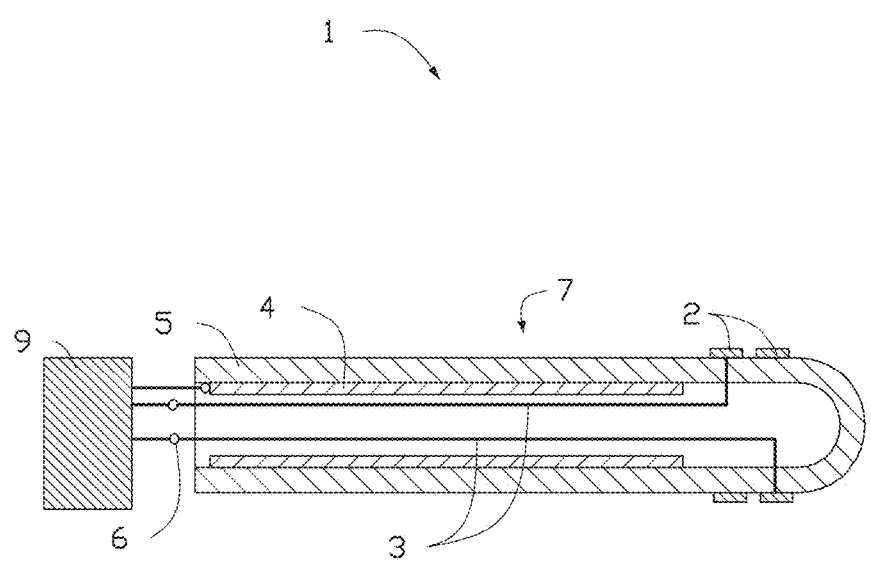
FIG. 1B is a schematic view of another embodiment of a medical device.
Figure 1C:
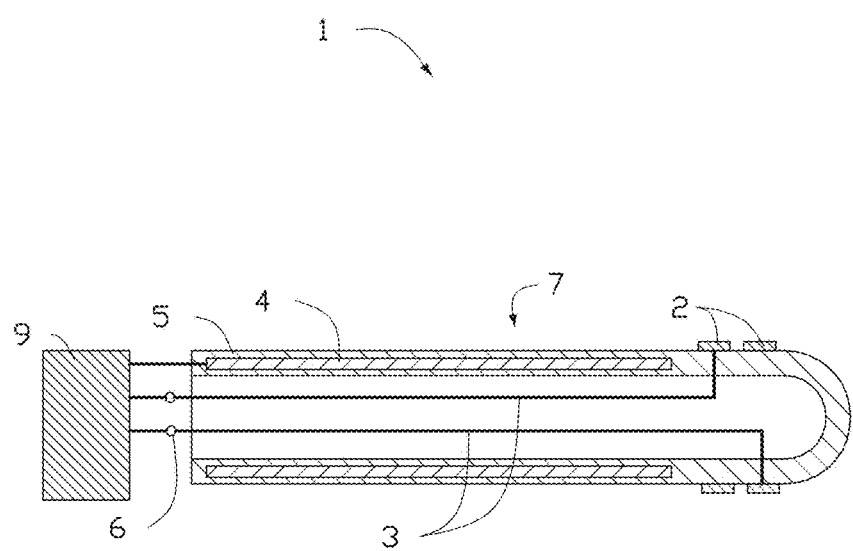
FIG. 1C is a schematic view of yet another embodiment of a medical device.
Figure 2:
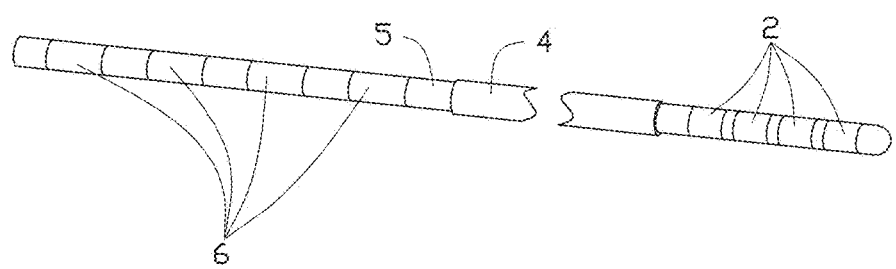
FIG. 2 is a schematic view of one embodiment of contactors and connectors.
Figure 3:
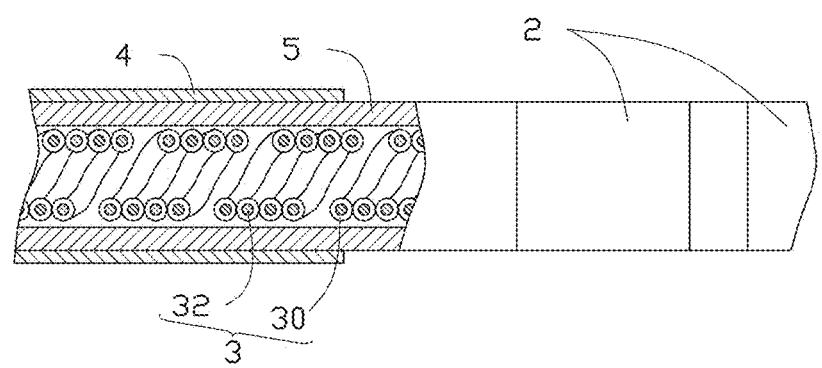
FIG. 3 is a schematic view of one embodiment of an arrangement of wires.

Referring to FIGS. 1-3, a medical device 1 of one embodiment includes an implantable lead 7 and a controller 9 electrically connected to the implantable lead 7.

The implantable lead 7 includes a pipe 5, a flexible conductive layer 4, at least one wire 3, at least one contactor 2 and at least one connector 6. The pipe 5 includes an annulus side wall and defines a hollow space. The flexible conductive layer 4 is located on the side wall of the pipe 5 and covers the middle portion of the pipe 5. The at least one wire 3 is located in the hollow space of the pipe 5. The at least one contactor 2 is located on a first end of the pipe 5, and the at least one connector 6 is located on a second end of the pipe 5 opposite to the first end. The at least one contactor 2 and the at least one connector 6 are electrically connected by the at least one wire 3.

The pipe 5 can be made of a flexible material such as polyurethane, silicone rubber, and nylon. The length, shape and diameter of the pipe 5 can be selected according to need. The pipe 5 is configured to support the contactor 2, the connector 6, and the flexible conductive layer 4 and protect the wires 3.

The connectors 6 can be in contact with the flexible conductive layer 4 or spaced from the flexible conductive layer 4. The connectors 6 are used to connect the controller 9 and the wires 3 or the controller 9 and the flexible conductive layer 4. The contactors 2 are spaced from and insulated from the flexible conductive layer 4. The contactors 2 are implanted in the biological tissue and used to connect the biological tissue and the wires 3. The shape and size of the contactors 2 can be selected according to the biological tissue. The number and order of the contactors 2 and the connectors 6 can be the same or different. In one embodiment, the number of the contactor 2 and the connector 6 are two as shown in FIG. 1A. The corresponding contactor 2 and the connector 6 are electrically connected by the wire 3. In one embodiment, the number of the contactor 2 is two, and the number of the connector 6 is three as shown in FIGS. 1B and 1C. The corresponding contactor 2 and the connector 6 are electrically connected by the wire 3. The excess one of the connector 6 is in contact with the flexible conductive layer 4 or electrically connected to the flexible conductive layer 4 by the wire 3.

In one embodiment, the implantable lead 7 includes four of the contactors 2 and four of the connectors 6 as shown in FIG. 2. The four contactors 2 are wrapped on an outer surface of the pipe 5 and spaced from each other. The four connectors 6 are also wrapped on an outer surface of the pipe 5 and spaced from each other. Both the four contactors 2 and four of the connectors 6 are columnar ring shaped. Alternatively, the number and shape of the contactors 2 and the connectors 6 can be selected according to application methods and electrical stimulation site. For example, the number of the contactors 2 and the connectors 6 can be six or eight, and the shape of the contactors 2 and the connectors 6 can be disc or spiral. This type of the implantable lead 7 can be used in a nerve stimulator, spinal cord stimulator and heart pacemaker.

The contactor 2 can made of platinum, platinum alloy, iridium, iridium alloy, titanium, titanium alloy, tungsten, stainless steel, carbon nanotubes, carbon fiber, or conductive polymer. In one embodiment, the contactor 2 is made of non-magnetic nano-material such as carbon nanotube film, carbon fiber or conductive polymer. The average resistivity of the contactor 2 made of non-magnetic nano-material is greater than $10^{-7}$ Ω·m such as $10^{-6}$ Ω·m, $10^{-5}$ Ω·m or $10^{-4}$ Ω·m. The contactor 2 can be made by wrapping a carbon nanotube film, carbon fiber or conductive polymer to form a single-layer structure or a multi-layer structure.

The wire 3 is configured to transmit electrical signals between the contactor 2 and the connector 6. The wire 3 can be made of conductive material such as platinum, iridium, platinum iridium alloy, stainless steel, carbon nanotubes, carbon fibers, or conductive polymer. The wire 3 can be linear or coiled into spiral. In one embodiment, the implantable lead 7 includes four of the wires 3 coiled into spiral as shown in FIG. 3. Each of the wires 3 includes a conductive core 32 and an insulative layer 30 wrapping the conductive core 32. The arrangement of the wires can increase the bending resistance, mechanical strength.

The flexible conductive layer 4 covers most of the inner surface or outer surface of the pipe 5. The flexible conductive layer 4 can be made of carbon nanotubes, graphene, carbon nanotubes based composite, graphene based composite. The carbon nanotubes based composite or graphene based composite can includes conductive polymer or biocompatible metal such as platinum, platinum alloy, iridium, iridium alloy, titanium, titanium alloy, tungsten, stainless steel, or MP35N. The carbon nanotubes and the graphene belong to the fullerene family and biocompatible. The surface of the carbon nanotubes and the graphene of the flexible conductive layer 4 can also be modified. The flexible conductive layer 4 can be a single-layer structure or a multi-layer structure. The flexible conductive layer 4 can be an undivided layer or a plurality of divided segments. The flexible conductive layer 4 can be continuous layer or discontinuous layer. The flexible conductive layer 4 can be located on the outer surface of the pipe 5 as shown in FIG. 1A, on the inner surface of the pipe 5 as shown in FIG. 1B, or embedded in the side wall of the pipe 5 as shown in FIG. 1C. The flexible conductive layer 4 can be insulated from the controller 9 as shown in FIG. 1A or electrically connected to a shell of the controller 9 as shown in FIG. 1B or FIG. 1C.

Figure 4:
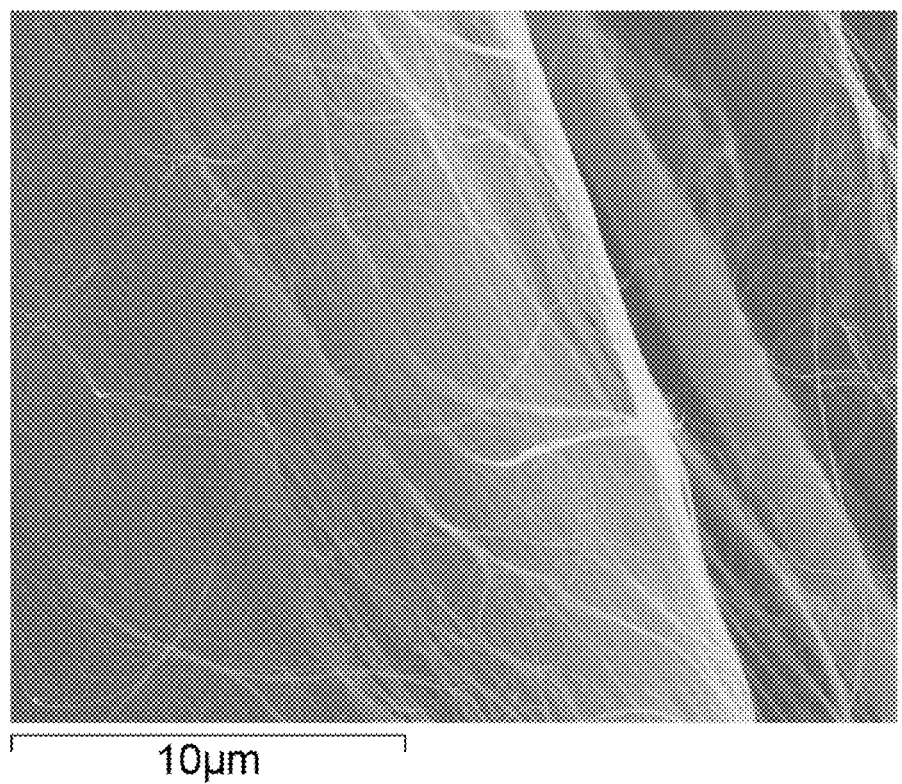
FIG. 4 is a Scanning Electron Microscope (SEM) image of one embodiment of a flexible conductive layer.

Referring to FIG. 4, a microstructure of a carbon nanotube material is shown. The carbon nanotube material includes a plurality of small carbon nanotubes or a plurality of carbon nanotube-based derivatives. The plurality of carbon nanotubes or carbon nanotube-based derivatives are stacked and combined with each other by van der Waals attractive force therebetween to form a macrostructure. The carbon nanotubes can have a modified surface. According to the number of graphene layer, the carbon nanotubes can be single-walled, double-walled, or multi-walled carbon nanotubes. The carbon nanotubes can be armchair, zigzag or chiral. The microstructure of the carbon nanotubes will affect the property of the carbon nanotubes. For example, the double-walled carbon nanotubes can have a higher conductivity easily, and the chirality of the carbon nanotubes will determine that the carbon nanotubes belong to a metal type or semiconductor type. The carbon nanotubes can be modified to obtain a surface with a carbonyl group, a carboxyl group or a hydroxyl group. The modification can be performed by a treatment such as oxidizing agent treating, heating and oxidation, plasma treating, esterification reaction, or amidation reaction. The aromatic ring-containing molecules can combined with the carbon nanotubes through a π bond stacking. The carbon nanotubes can be encapsulated by a polymer shell or doped with other material. The above provided carbon nanotubes can be made into a macrostructure with good mechanical and electrical properties.

The graphene is a planar sheet of carbon atoms arranged in a hexagonal pattern to form a two-dimensional honeycombed structure. The graphene has excellent mechanical and electrical properties. The graphene can be used to make a graphane and a graphene oxide, and a graphene oxide with modified surface. In addition, the graphene and the graphene with modified surface can be combined with nanoparticles, polymer or carbon-based materials to form a composite.

Figure 5A:
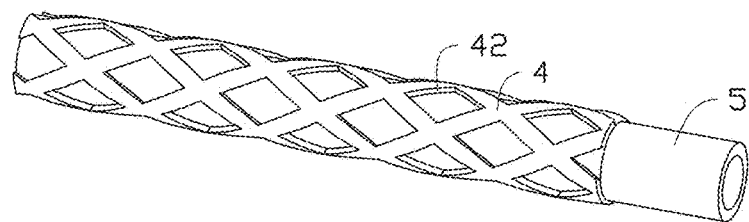
FIG. 5A is a schematic view of one embodiment of a flexible conductive layer.

In one embodiment, the flexible conductive layer 4 is a hollow undivided film as shown in FIG. 5A. The hollow undivided flexible conductive layer 4 defines a plurality of holes 40. The hole 40 can be any shape such as round, square, rhombus, or triangle. The size of the holes 40 can be selected according to need. The flexible conductive layer 4 can be a carbon nanotube film or graphene sheet wrapped around the pipe 5. The flexible conductive layer 4 which is hollow and undivided can save the flexible conductive material to reduce the cost and improve the fatigue resistance without significantly influence the reduction of the RF heating.

Figure 5B:
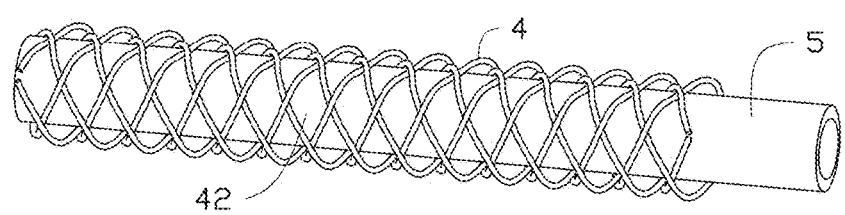
FIG. 5B is a schematic view of another embodiment of a flexible conductive layer.

In one embodiment, the flexible conductive layer 4 is a mesh including a plurality of flexible conductive wires weaved or crossed with each other as shown in FIG. 5B. The flexible conductive layer 4 with mesh structure defines a plurality of holes 40. The flexible conductive wires can be carbon nanotube wires, carbon nanotube based composite wires or graphene based composite wires. Alternatively, the flexible conductive layer 4 can be formed by wrapping a single flexible conductive wire around the pipe 5. The flexible conductive layer 4 with mesh structure is easy to be fabricated.

Figure 5C:
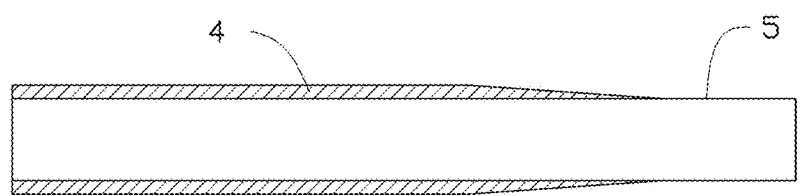
FIG. 5C is a schematic view of yet another embodiment of a flexible conductive layer.

In one embodiment, the flexible conductive layer 4 has a thickness gradient as shown in FIG. 5C. The thickness of the edge of the flexible conductive layer 4 gradually decreases to zero so that a smooth transition is formed between the flexible conductive layer 4 and the pipe 5. Thus, the mechanical friction of the flexible conductive layer 4 can be reduced and the protection to the flexible conductive layer 4 is improved. The thickness of the flexible conductive layer 4 in different positions can be selected according to the degree of RF field interaction along the implantable lead 7. For example, the thickness of the flexible conductive layer 4 is increased at the position where the RF heating is strong.

The flexible conductive layer 4 can be formed by non-uniformly wrapping a carbon nanotube film, a carbon nanotube wire, a carbon nanotube based composite wire, or a graphene based composite wire around the pipe 5.

Figure 5D:
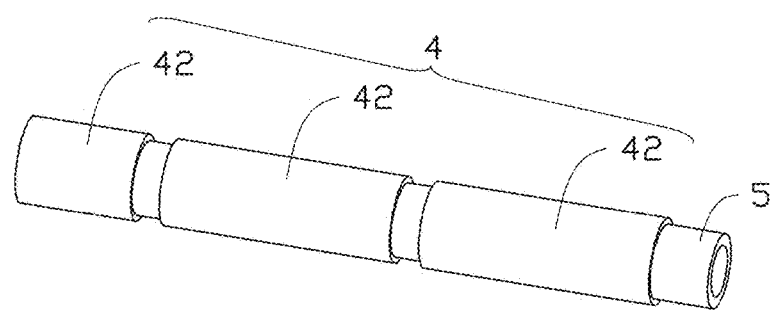
FIG. 5D is a schematic view of yet another embodiment of a flexible conductive layer.

In one embodiment, the flexible conductive layer 4 is divided and includes a plurality of flexible conductive segments 42 as shown in FIG. 5D. The plurality of flexible conductive segments 42 can be insulated from each other or electrically connected by wires. The flexible conductive layer 4 which is divided can improve the bending fatigue resistance without significantly influence the inhibitory effect of the RF heating. None of the flexible conductive segments 42 on the position of the pipe 5 where need to bend seriously. The plurality of flexible conductive segments 42 can be spaced from or overlapped with each other.

Furthermore, the flexible conductive layer 4 can have at least two kinds of structures as shown in FIGS. 1A-1D and described above. Because the implantable lead 7 may be in different magnetic environment of MRI, the flexible conductive layer 4 can have different structures.

The controller 9 is configured to receive an input electrical signal from the implantable lead 7 or output a voltage or current to the implantable lead 7. The controller 9 can have a conductive shell which has a relatively very large area. The medical device 1 can be a heart pacemaker a defibrillator, deep brain stimulator, spinal cord stimulator, vagus nerve stimulator, sacral nerve stimulator, stomach stimulator, or bladder stimulator.

In use of the medical device 1, the medical device 1 can be implanted in and contact with the biological tissue such as heart. The controller 9 can detect and receive an input electrical signal such as electrocardiogram (ECG) signal from the contactors 2 and output a voltage or current signal such as a pacemaking or defibrillating signal to the contactors 2. Because the implantable lead 7 has a slender structure, it is easy to produce an induced current in the wires 3 in the RF magnetic field of the MRI. The induced current flows to the biological tissue through the contactors 2 and will cause a severe RF heating at the contactors 2. The flexible conductive layer 4 can reduce or even eliminate the RF heating effectively as described below.

Figure 6A:
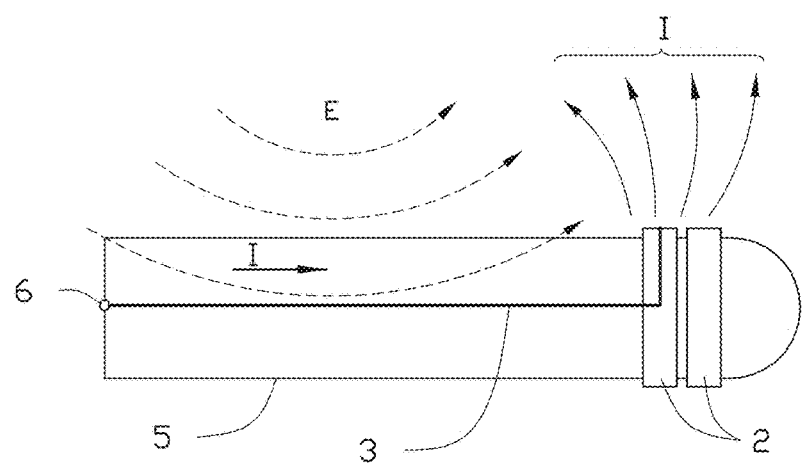
FIG. 6A is a schematic view of one embodiment of a principle of producing a RF heating.
Figure 6B:
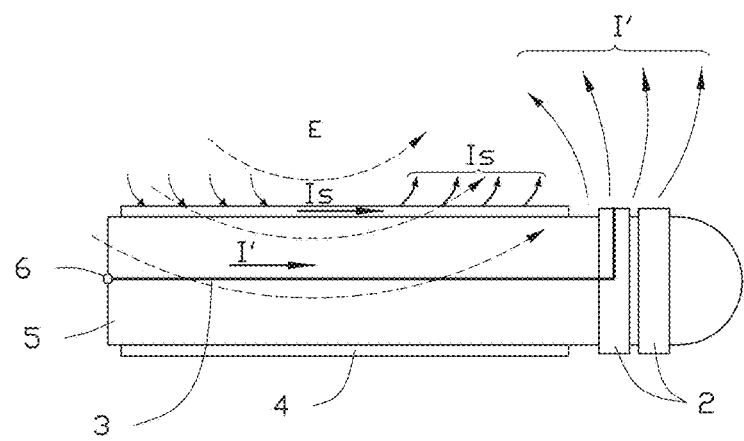
FIG. 6B is a schematic view of another embodiment of a principle of reducing the RF heating of FIG. 6A.

As shown in FIG. 6A, the RF alternating magnetic field in MRI will induce an alternating electric field E in according to Faraday's law of electromagnetic induction, and thus, an alternating electric current I is induced in the wires 3. As shown in FIG. 6B, when a flexible conductive layer 4 is applied, most of the induced electric current will be dispersed in the flexible conductive layer 4 to form an induced electric current Is due to the Skin Effect, thus the induced electric current in the wires 3 will be reduced to much smaller electric current I'. That is, the RF heating at the contactors 2 will be reduced significantly. When the flexible conductive layer 4 is located on the outer surface of the pipe 5 as shown in FIG. 1A, the flexible conductive layer 4 will be in contact with the biological tissue after implantation in the biological tissue. Thus, the induced electric current Is in the flexible conductive layer 4 will flow to the biological tissue through the entire flexible conductive layer 4. Because the flexible conductive layer 4 has a large contacting surface with the biological tissue, especially due to the large specific surface of the carbon nanotube, the current density flowing to the biological tissue is very small. When the flexible conductive layer 4 is electrically connected to the shell of the controller 9 as shown in FIG. 1B-1C, the induced electric current Is in the flexible conductive layer 4 will be conducted to the conductive shell of the controller 9 which has a relatively very large area and flow to the biological tissue through the shell of the controller 9 with a very small current density. Thus, the RF heating of the MRI can be reduced.

The thickness of the flexible conductive layer 4 is related to the material of the flexible conductive layer 4. To obtain the same inhibitory effect on the RF heating, the lower resistivity is; the smaller the thickness of the flexible conductive layer 4 is needed. The theoretical resistivity of the carbon nanotubes is $0.8\times10^{-8}$ Ω·m which is lower than the resistivity of copper of $1.68\times10^{-8}$ Ω·m. It is reported that the resistivity of the carbon nanotube fiber or film is in a range from about $10^{-7}$ Ω·m to about $10^{-2}$ Ω·m. The average resistivity of the carbon nanotube fiber or film may reach the order of magnitude of $10^{-8}$ Ω·m. According to the Skin Effect, a current conduction along only the outer surface of a conductor at high frequencies. The Skin depth δ satisfies the formula:

$$\delta = \sqrt{\frac{\rho}{\pi f \mu_R \mu_0}}$$

where, the ρ represents the resistivity of the conductor, the unit of the resistivity ρ is Ω·m; the f represents the frequency of the current, the unit of the frequency f is Hz; the $\mu_R$ represents the relative magnetic permeability and is a constant; the to represents the magnetic permeability of vacuum, $\mu_0$=4 $\pi\times10^{-7}$ H/m. According to the formula above, the thickness of the flexible conductive layer 4 is proportional to the square root of the resistivity of the flexible conductive layer 4. That is, the flexible conductive layer 4 with the thickness in a range from about 1 micrometer to about 2 millimeters can obtain a good shielding effect. Because the DC resistance of the wires 3 is usually in a range from about a few ohms to about several hundred ohms, the DC resistance of the flexible conductive layer 4 in its entirety and in the undivided form should be less than 1 kΩ. The DC resistance of the flexible conductive layer 4 in its entirety and in the undivided form is less; the shielding effect is better. The average line resistance ratio of the flexible conductive layer 4 is less than 20 Ω/mm, namely, the DC resistance of the flexible conductive layer 4 along the length direction in each millimeter is less than 20Ω.

Figure 7:
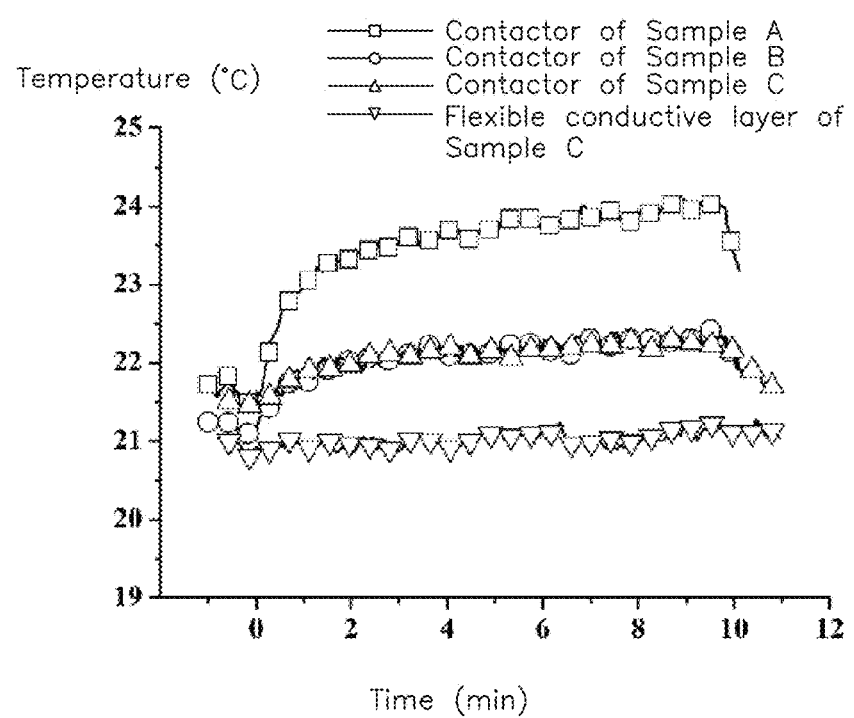
FIG. 7 show testing results of implantable leads of various embodiments.

Referring to FIG. 7, experiment testing results of the samples A-C of the implantable leads 7 are shown. The samples A-C of the implantable leads 7 have the structure of FIG. 1A and FIG. 2 except that the sample A has none of the flexible conductive layer 4. The pipes 5 of the samples A-C are made of polyurethane, the wires 3 are made of stainless steel core with insulating layer and arranged in the structure of FIG. 3, the contactor 2 and the connector 6 are made of stainless steel, and the flexible conductive layers 4 are made of carbon nanotube film having carbon nanotubes with surface modified in the structure of FIG. 5C. The MRI scan time is about 9.8 minutes. The line of □ shows the temperature of the contactor 2 of the sample A. The lines of ○ and Δ show the temperature of the contactor 2 of the samples B and the sample C. The line of ∇ shows the temperature of the flexible conductive layer 4 of the sample C. As shown in FIG. 7, the temperature of the contactor 2 of the samples B and the sample C reduce 50% compare to the sample A. The temperature of the flexible conductive layer 4 of the sample C does not rise significantly.

A method for making the implantable lead 7 of one embodiment includes following steps:

step (a), providing a pipe 5;

step (b), forming a flexible conductive layer 4 on a surface of the pipe 5;

step (c), applying at least one contactor 2 on a first end of the pipe 5;

step (d), applying the at least one connector 6 on a second end of the pipe 5 opposite to the first end;

step (e), placing the at least one wire 3 in the pipe 5 to electrically connect the at least one contactor 2 and the at least one connector 6.

In step (a), the pipe 5 can be made of a flexible material such as polyurethane, silicone rubber, and nylon.

In step (b), the flexible conductive layer 4 can be formed on an outer surface of the pipe 5 by coating a paste of carbon nanotubes or graphene, depositing a layer of carbon nanotubes or graphene, or wrapping a film, a ribbon, a fiber, a yarn or a wire of carbon nanotubes or graphene. The forming the flexible conductive layer 4 includes forming the flexible conductive layer 4 which is hollow and undivided as shown in FIG. 5A, forming the flexible conductive layer 4 with mesh structure as shown in FIG. 5B, forming the flexible conductive layer 4 with a thickness gradient as shown in FIG. 5C, or forming the divided flexible conductive layer 4 as shown in FIG. 5D.

In one embodiment, the film, ribbon, fiber, yarn or wire of carbon nanotubes can be made by dry-spinning or wet-spinning from a carbon nanotube solution. For example, the fine carbon nanotubes are uniformly dispersed into a first solvent, such as an aqueous solution of sodium dodecyl sulfate (SDS), to form a first solution. The first solution is then applied into a second solvent, such as a polyvinyl acetate (PVA) polymer solution, to condense and obtain a second solution. Then the ribbon or fibers of carbon nanotubes can be obtained by rotating and pulling the second solution.

In one embodiment, the film, ribbon, fiber, yarn or wire of carbon nanotubes can be made by spinning from a carbon nanotube array. For example, a super aligned carbon nanotube array is grown on a substrate coated with catalyst by chemical vapor deposition (CVD). The substrate can be a silicon wafer coated with ferrocene as catalyst. Then a carbon nanotube film or yarn is drawn from the carbon nanotube array. The carbon nanotube film or yarn includes a plurality of carbon nanotubes combined by van der Waals forces. The carbon nanotube film or yarn can be further twisted by a mechanical force, shrunk by a solvent, or infiltrated with polymer.

In one embodiment, the film, ribbon, fiber, yarn or wire of carbon nanotubes can be made by spinning from a carbon nanotube air gel. For example, the CNTY or the carbon nanotube ribbon is fabricated in a reaction furnace by floating catalyst vapor deposition. The carrier gas is hydrogen. The catalyst, the growth agent, and the carbon source gas are mixed in proportion and introduced into the reaction furnace to form the air gel. The catalyst can be ferrocene, the growth agent can be thiophene, and the carbon source gas can be hexane, ethanol, or xylene. The air gel is heated to a pyrolysis temperature to grow aggregated carbon nanotubes. The CNTY or the carbon nanotube ribbon can be obtained by capturing or winding the aggregated carbon nanotubes. The CNTY or the carbon nanotube ribbon can be further twisted, rolled or stranded to form a carbon nanotube film.

In step (c), the at least one contactor 2 is formed on the outer surface of the pipe 5 and spaced from the flexible conductive layer 4. The at least one contactor 2 can be mad by coating, depositing or plating.

Figure 8A:
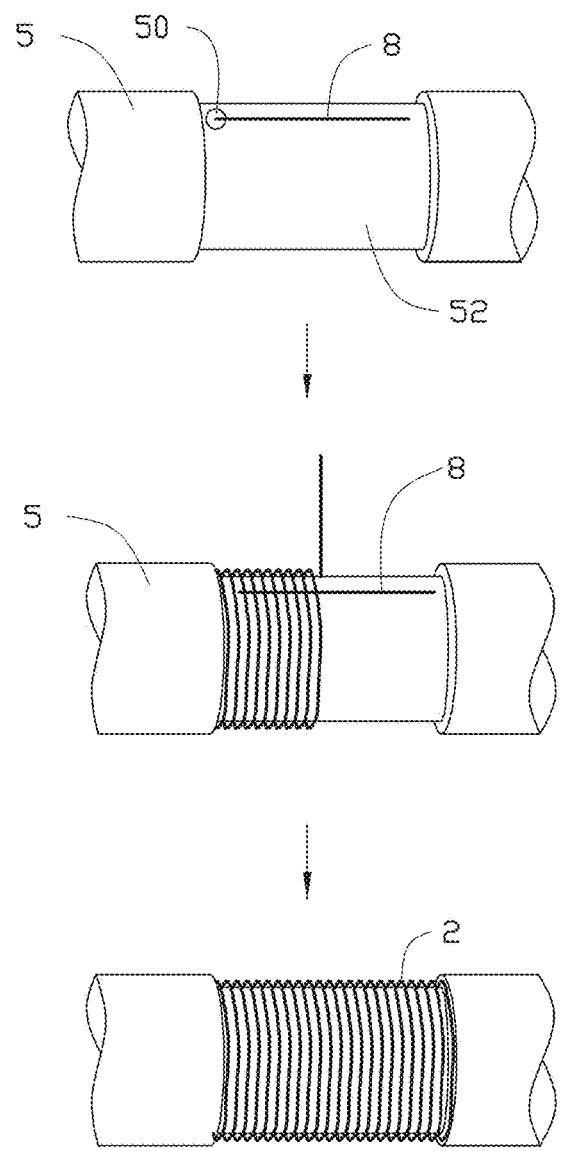
FIG. 8A is a flow chart of one embodiment of a method for making a contactor.
Figure 8B:
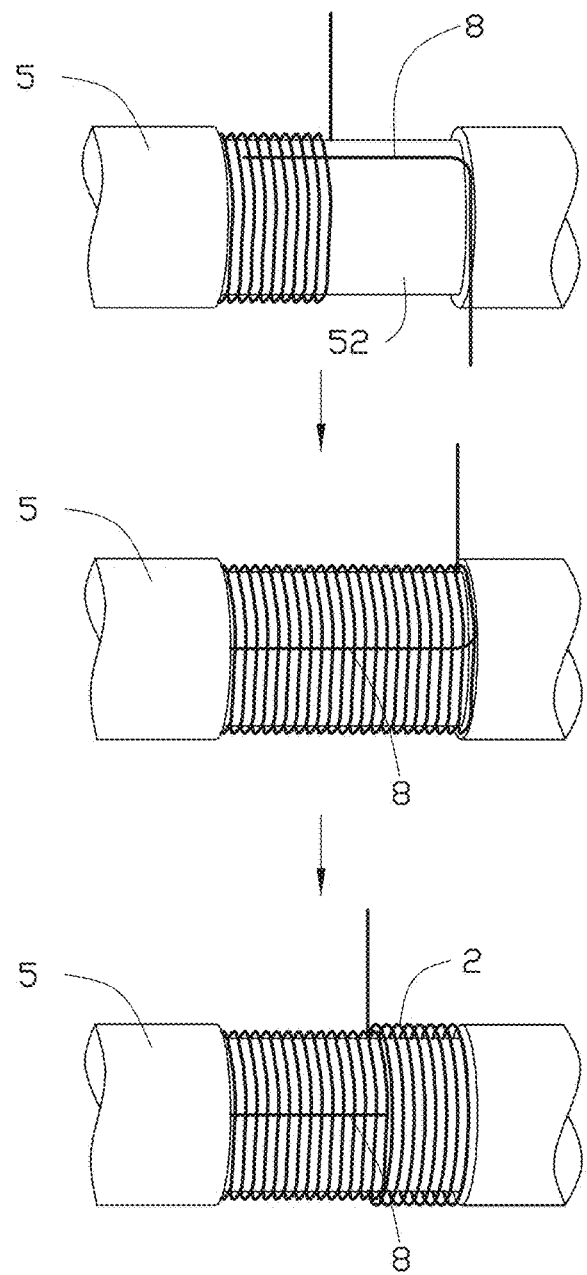
FIG. 8B is a flow chart of another embodiment of a method for making a contactor.

As shown in FIGS. 8A-8B, in one embodiment, the contactor 2 is made by the following steps:

step (c1), extending a portion of the wire 3 out of the pipe 5 to form an exposed portion 8;

step (c2) wrapping a carbon nanotube film or carbon fiber on the exposed portion 8 of the wire 3 to form a the contactor 2.

In step (c1), the exposed portion 8 can be wrapped around the outer surface of the pipe 5 or located on the outer surface of the pipe 5 in parallel with the pipe 5. Furthermore, a hole 50 and a groove 52 can be formed in the pipe 5 before extending the wire 3 out of the pipe 5. The groove 52 is around the pipe 5 and the hole 50 is in the groove 52. The groove 52 and the hole 50 can be formed by machine cutting or thermoplastic molding. Furthermore, a metal layer can be formed on the groove 52 by plating sputtering or deposition to increase the connectivity between the exposed portion 8 and the contactor 2.

In step (c2), the carbon nanotube film or carbon fiber is in contact with the exposed portion 8. The contactor 2 packs and covers the exposed portion 8. The contactor 2 can be a single-layer or a multi-layer structure. Furthermore, as shown in FIG. 8B, the exposed portion 8 can be folded to form a U shaped configuration and sandwiched between two layers of the contactor 2. Furthermore, a biocompatible paste can be applied to bond the exposed portion 8 and the contactor 2 after wrapping.

In step (d), the at least one connector 6 is formed on the outer surface of the pipe 5 and spaced from the flexible conductive layer 4.

In step (e), the at least one wire 3 can be electrically connect to the at least one contactor 2 or the at least one connector 6 by pressing, screws, tying, bonding, laser welding, resistance spot welding, brazing welding, or ultrasonic welding.

Furthermore, it is found that the contactor 2 made of non-magnetic nano-material such as carbon nanotube film, carbon fiber or conductive polymer shows an excellent performance for reducing field distortion in MRI which leads to artifacts that will lower the local image quality and cause inconvenience or interference compare with the contactor 2 made of metal or alloy.

Figure 9:
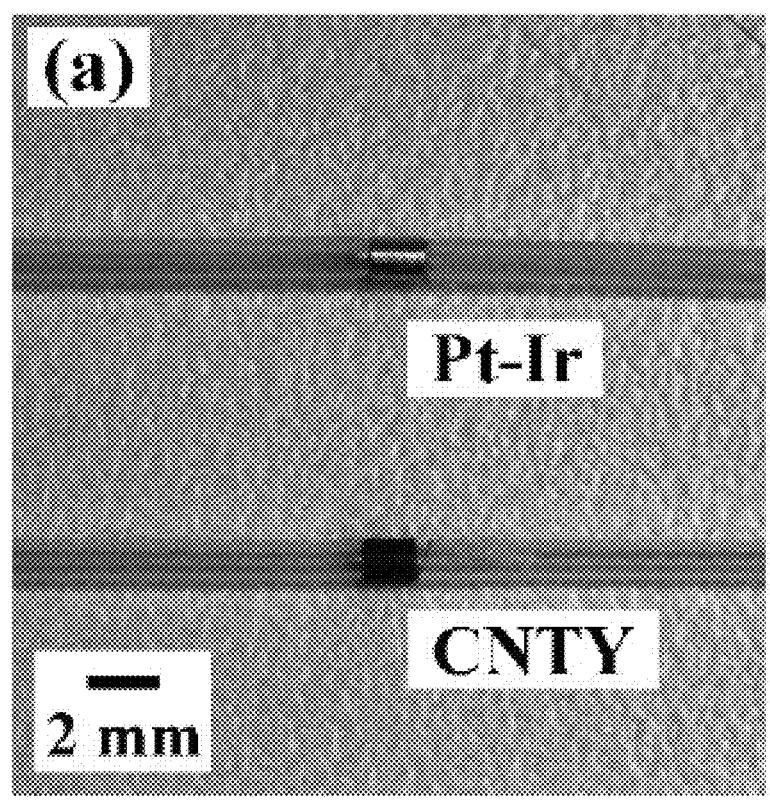
FIG. 9 is an image of one embodiment of a carbon nanotube yarn (CNTY) implantable lead and a Pt—Ir implantable lead.

In testing, the contactor 2 made of CNTY and the contactor 2 made of Pt—Ir alloy are prepared. The CNT yarns are wrapped tightly onto a polyurethane (PU) pipe with an outer diameter of 1.3 millimeters and formed a 1.5 millimeters long cylindrical surface to form the CNTY implantable lead. The same PU pipe is sleeved with a Pt—Ir alloy (90% of Pt and 10% of Ir) tube with an outer diameter of 1.3 millimeters and formed a 1.5 millimeters long cylindrical surface form the Pt—Ir implantable lead. Both the CNTY implantable lead and the Pt—Ir implantable lead have the similar structure as DBS leads used in clinical practice and shown in FIG. 9.

A polymethyl methacrylate (PMMA) phantom with inner dimensions of 320 mm×160 mm×120 mm is used, and filled to a height of approximately 60 millimeters with 0.9% saline doped with 1.25 g/L $CuSO_4$ to shorten relaxation times to convenient values. Both the CNTY implantable lead and the Pt—Ir implantable lead are suspended in the middle of the solution by holding the PU pipe with PMMA frames.

Figure 10:
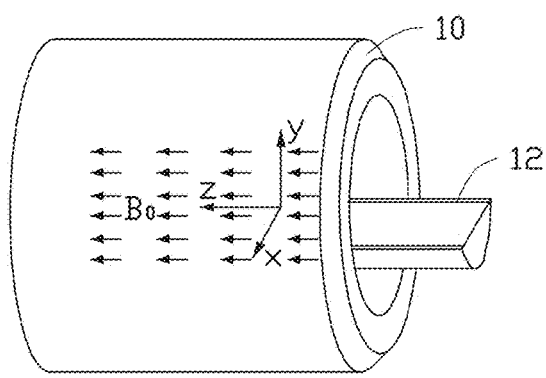
FIG. 10 is a schematic view of one embodiment of a MRI scanning system.

A multi-transmit MRI scanner 10 featuring a maximal gradient strength of 40 mT/m and maximal slew-rates of 200 T/m/s is used to acquire the images. The nominal frequency of the RF system is 127.73 MHz. FIG. 10 shows a schematic diagram of a MRI scanning system including the multi-transmit MRI scanner 10 and the patient table 12, and direction of the static magnetic field $B_0$ is defined as z-axis. The Q-body coil is used for both RF excitation and signal detection. Both spin-echo (SE) and gradient-echo (GE) protocols are applied. Images are acquired with the samples oriented parallel to the z-axis as well as the x-axis respectively at the isocenter of the multi-transmit MRI scanner 10 bore.

Figures 11A, 11B, 11C, 11D:
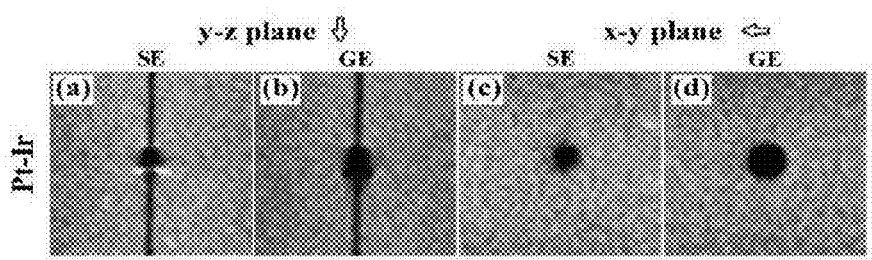
FIG. 11A to FIG. 11H show Magnetic resonance (MR) images of a CNTY implantable lead and a Pt—Ir implantable lead.
Figures 11E, 11F, 11G, 11H:
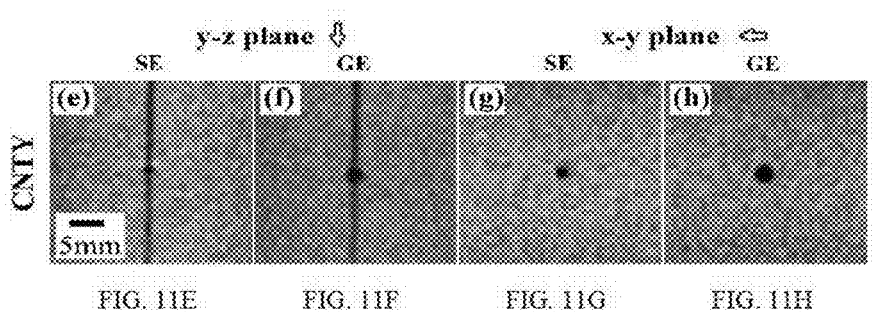

FIG. 11A to FIG. 11H show MR images of CNTY implantable lead and Pt—Ir implantable lead oriented along the z-axis at the isocenter of the multi-transmit MRI scanner 10 bore. And generally the CNTY implantable lead revealed clearly a better performance in terms of signal distortion severity. On x-y plane images as shown in FIG. 11A and FIG. 11B, the Pt—Ir implantable lead obviously exhibited a characteristic spear-shaped artifact pointing along the frequency encoding direction. This is associated with magnetic field distortion caused by susceptibility difference. The artifact of the CNTY implantable lead is largely reduced as shown in FIG. 11E and FIG. 11F. And the artifact size determined from x-y plane image are 2.9 millimeters compared to 5.9 millimeters for Pt—Ir under GE sequences. Because SE sequence adopted a 180° refocusing pulse that could recover some of the signal loss due to spin dephasing, the artifact size of the CNTY implantable lead could be further reduced, to 1.8 millimeters in comparison to 3.6 millimeters for Pt—Ir. This is only slightly greater than 1.4 millimeters, the artifact size of the PU pipe, and is very close to its real dimension. It would be beneficial in the case that the vicinity of the implantable lead is in the need of examination.

Figure 12:
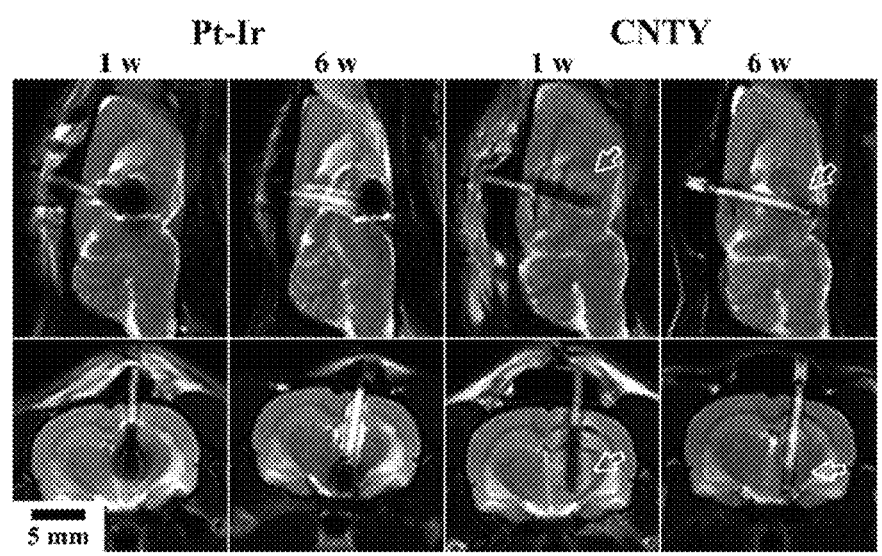
FIG. 12 shows MR images of rats after implantations of CNTY implantable leads or Pt—Ir implantable leads.

The images of the rats after implantation are shown in FIG. 12. In accordance with in vitro results, the Pt—Ir implantable lead exhibited severe artifact in vivo that made it impossible to identify the structures around the lead. At the mean time the CNTY implantable lead revealed little signal distortion so that the acute edema in the vicinity of the lead caused by implantation within one week could be seen clearly which healed after 6 weeks.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A method for making an implantable lead, the method comprising:
   providing a pipe comprising a first end portion, a second end portion opposite to the first end portion, and a middle portion connecting the first end portion and the second end portion;
   forming a flexible conductive layer on the middle portion of the pipe, the flexible conductive layer having a mesh structure with a plurality of flexible conductive wires;
   placing at least one connecting wire in the pipe;
   applying at least one contactor on the first end portion of the pipe, comprising:

extending a portion of the at least one connecting wire out from the pipe to form an exposed portion; and wrapping a carbon nanotube film on the exposed portion of the at least one connecting wire to form the at least one contactor;

applying at least one connector on the second end portion of the pipe; and electrically-connecting the at least one contactor and the at least one connector with at least one connecting wire inside of the pipe.

2. The method of claim 1, wherein the pipe is made of a flexible material selected from the group consisting of polyurethane, silicone rubber, and nylon.

3. The method of claim 1, wherein forming the flexible conductive layer on the middle portion of the pipe comprises coating a paste of carbon nanotubes or graphene, depositing a layer of carbon nanotubes or graphene, or wrapping a film, a ribbon, a fiber, a yarn or a wire of carbon nanotubes or graphene on the middle portion of the pipe.

4. The method of claim 1, wherein the flexible conductive layer is formed on an outer surface of the pipe, an inner surface of the pipe, embedded in a side wall of the pipe, or combinations thereof.

5. The method of claim 1, wherein a thickness of the flexible conductive layer is in a range from about 1 micrometer to about 2 millimeters.

6. The method of claim 1, wherein an average line resistance ratio of the flexible conductive layer is less than 20 $\Omega$/mm.

7. The method of claim 1, wherein the at least one contactor comprises a material selected from the group consisting of platinum, platinum alloy, iridium, iridium alloy, titanium, titanium alloy, tungsten, stainless steel, carbon nanotubes, carbon fiber, and conductive polymer.

8. The method of claim 1, wherein an average resistivity of the at least one contactor is greater than $10^{-6}$ $\Omega \cdot$m.

9. The method of claim 1, further comprising:
making a groove around the pipe; and
placing the exposed portion in the groove.

10. The method of claim 9, further comprising forming a metal layer on the groove by plating, sputtering or deposition.

11. The method of claim 1, further comprising:
folding the exposed portion to form a U-shaped configuration; and
sandwiching the exposed portion between two layers of the at least one contactor.

12. The method of claim 1, wherein the carbon nanotube film comprises a plurality of carbon nanotubes combined by van der Waals forces.

13. The method of claim 1, further comprising drawing the carbon nanotube film from a carbon nanotube array thereby forming the carbon nanotube film.

* * * * *